US012708773B2

(12) United States Patent
Huertas Fernandez et al.

(10) Patent No.: US 12,708,773 B2
(45) Date of Patent: Aug. 18, 2026

(54) METHOD AND APPARATUS FOR CONTROLLING NEUROSTIMULATION BASED ON PATIENT LIFE FACTORS

(71) Applicant: Boston Scientific Neuromodulation Corporation, Valencia, CA (US)

(72) Inventors: Ismael Huertas Fernandez, Seville (ES); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 245 days.

(21) Appl. No.: 18/756,586

(22) Filed: Jun. 27, 2024

(65) Prior Publication Data

US 2024/0342482 A1 Oct. 17, 2024

Related U.S. Application Data

(63) Continuation of application No. 16/736,580, filed on Jan. 7, 2020, now Pat. No. 12,059,566.

(Continued)

(51) Int. Cl.

*A61N 1/36* (2006.01)
*A61N 1/02* (2006.01)
*A61N 1/372* (2006.01)

(52) U.S. Cl.

CPC ......... *A61N 1/36132* (2013.01); *A61N 1/025* (2013.01); *A61N 1/36135* (2013.01); *A61N 1/37247* (2013.01)

(58) Field of Classification Search

CPC .............. A61N 1/3605; A61N 1/36071; A61N 1/36128; A61N 1/36132; A61N 1/36135; A61N 1/37235

See application file for complete search history.

(56) References Cited

U.S. PATENT DOCUMENTS 7,647,116 B2 1/2010 Bauhahn
9,333,350 B2 5/2016 Rise et al.

(Continued)

OTHER PUBLICATIONS

"U.S. Appl. No. 16/736,580, Advisory Action mailed Jan. 25, 2024", 3 pgs.

(Continued)

*Primary Examiner* — Eugene T Wu
(74) *Attorney, Agent, or Firm* — Schwegman Lundberg & Woessner, P.A.

(57) ABSTRACT

An example of a system for controlling delivery of neurostimulation from a stimulation device to a patient according to a selected neurostimulation program may include a programming device. The programming device may be configured to be communicatively coupled to the stimulation device and to select the neurostimulation program. The programing device may include a user interface and a program selection circuit. The program selection circuit may be configured to receive life factor information indicative of at least one of an environmental factor and a biopsychosocial factor of the patient, to select the neurostimulation program from a plurality of neurostimulation programs based on the received life factor information, to present a recommendation using the user interface based on the selected neurostimulation program, and to receive a user command responding to the recommendation using the user interface.

20 Claims, 10 Drawing Sheets

Related U.S. Application Data

(60) Provisional application No. 62/789,867, filed on Jan. 8, 2019.

(56) References Cited

U.S. PATENT DOCUMENTS

| | | | | |
|---|---|---|---|---|
| 2002/0169636 | A1* | 11/2002 | Eggers | A61B 5/411 705/3 |
| 2009/0264954 | A1 | 10/2009 | Rise et al. | |
| 2010/0114237 | A1 | 5/2010 | Denison et al. | |
| 2013/0218232 | A1 | 8/2013 | Giftakis et al. | |
| 2016/0361543 | A1 | 12/2016 | Kaula et al. | |
| 2017/0056642 | A1 | 3/2017 | Moffitt et al. | |
| 2017/0080234 | A1 | 3/2017 | Gillespie et al. | |
| 2017/0368344 | A1 | 12/2017 | Ironi et al. | |
| 2018/0085055 | A1 | 3/2018 | Annoni et al. | |
| 2018/0110464 | A1* | 4/2018 | Annoni | A61B 5/4824 |
| 2018/0169411 | A1 | 6/2018 | Goodall et al. | |
| 2018/0192943 | A1 | 7/2018 | Annoni et al. | |
| 2018/0193652 | A1 | 7/2018 | Srivastava et al. | |
| 2019/0151654 | A1* | 5/2019 | Wingeier | A61N 1/08 |
| 2020/0215330 | A1 | 7/2020 | Huertas Fernandez et al. | |

OTHER PUBLICATIONS

"U.S. Appl. No. 16/736,580, Advisory Action mailed Mar. 6, 2023", 4 pgs.
"U.S. Appl. No. 16/736,580, Advisory Action mailed Mar. 24, 2022", 5 pgs.
"U.S. Appl. No. 16/736,580, Examiner Interview Summary mailed Jan. 12, 2024", 2 pgs.
"U.S. Appl. No. 16/736,580, Examiner Interview Summary mailed Sep. 22, 2023", 2 pgs.
"U.S. Appl. No. 16/736,580, Examiner Interview Summary mailed Oct. 18, 2022", 2 pgs.
"U.S. Appl. No. 16/736,580, Examiner Interview Summary mailed Nov. 22, 2021", 3 pgs.
"U.S. Appl. No. 16/736,580, Final Office Action mailed Jan. 10, 2023", 9 pgs.
"U.S. Appl. No. 16/736,580, Final Office Action mailed Jan. 25, 2022", 13 pgs.
"U.S. Appl. No. 16/736,580, Final Office Action mailed Nov. 15, 2023", 12 pgs.
"U.S. Appl. No. 16/736,580, Non Final Office Action mailed Jul. 5, 2023", 10 pgs.
"U.S. Appl. No. 16/736,580, Non Final Office Action mailed Aug. 1, 2022", 9 pgs.
"U.S. Appl. No. 16/736,580, Non Final Office Action mailed Aug. 30, 2021", 17 pgs.
"U.S. Appl. No. 16/736,580, Notice of Allowance mailed Apr. 8, 2024", 8 pgs.
"U.S. Appl. No. 16/736,580, Response filed Jan. 10, 2024 to Final Office Action mailed Nov. 15, 2023", 15 pgs.
"U.S. Appl. No. 16/736,580, Response filed Feb. 22, 2023 to Final Office Action mailed Jan. 10, 2023", 12 pgs.
"U.S. Appl. No. 16/736,580, Response filed Feb. 28, 2022 to Final Office Action mailed Jan. 25, 2022", 12 pgs.
"U.S. Appl. No. 16/736,580, Response filed Apr. 25, 2022 to Advisory Action mailed Mar. 24, 2022", 14 pgs.
"U.S. Appl. No. 16/736,580, Response filed May 9, 2023 to Advisory Action mailed Mar. 6, 2023", 12 pgs.
"U.S. Appl. No. 16/736,580, Response filed Sep. 19, 2023 to Non Final Office Action mailed Jul. 5, 2023", 12 pgs.
"U.S. Appl. No. 16/736,580, Response filed Oct. 27, 2022 to Non Final Office Action mailed Aug. 1, 2022", 13 pgs.
"U.S. Appl. No. 16/736,580, Response filed Nov. 23, 2021 to Non Final Office Action mailed Aug. 30, 2021", 13 pgs.
Funakubo, M., et al., "The inner ear is involved in the aggravation of nociceptive behavior induced by lowering barometric pressure of nerve injured rats", European Journal of Pain 14 (2010) 32-39.
Gatchel, Robert J., et al., "The Biopsychosocial Approach to Chronic Pain: Scientific Advances and Future Directions", Psychological Bulletin, 2007, vol. 133, No. 4, 581-624.
Palermo, Tonya M., et al., "Subjective Sleep Disturbances in Adolescents With Chronic Pain: Relationship to Daily Functioning and Quality of Life", The Journal of Pain, vol. 6, No. 3, (Mar. 2995), 201-207.
Sato, Jun, et al., "Low barometric pressure aggravates neuropathic pain in guinea pigs", Neuroscience Letters 503 (2011) 152-156.
Sato, Jun, "Weather change and pain: a behavioral animal study of the influences of simulated meteorological changes on chronic pain", Int J Biometeorol, 47:55-61, Jan. 30, 2003.

* cited by examiner

METHOD AND APPARATUS FOR CONTROLLING NEUROSTIMULATION BASED ON PATIENT LIFE FACTORS

CLAIM OF PRIORITY

This application is a continuation of U.S. patent application Ser. No. 16/736,580, filed on Jan. 7, 2020, which claims the benefit of priority under 35 U.S.C. § 119 (e) of U.S. Provisional Patent Application Ser. No. 62/789,867, filed on Jan. 8, 2019, which are herein incorporated by reference in their entireties.

TECHNICAL FIELD

This document relates generally to medical devices and more particularly to a method and system for controlling delivery of neurostimulation based on patient life factors such as biopsychosocial, environmental, and/or physical factors.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

Programs and delivery times of neurostimulation can be selected based on the patient's condition(s) indicated for the treatment. It has been observed, however, that efficacy of neurostimulation can be affected by the patient's physical and mental states as well as environmental factors. Thus, after initial settings, delivery of the neurostimulation may need to be adjusted as needed by the patient for maintaining efficacy and/or optimization of the therapy.

SUMMARY

An example (e.g., "Example 1") of a system for controlling delivery of neurostimulation from a stimulation device to a patient according to a selected neurostimulation program may include a programming device. The programming device may be configured to be communicatively coupled to the stimulation device and to select the neurostimulation program. The programing device may include a user interface and a program selection circuit. The program selection circuit may be configured to receive life factor information indicative of at least one of an environmental factor or a biopsychosocial factor of the patient, to select the neurostimulation program from a plurality of neurostimulation programs based on the received life factor information, to present a recommendation using the user interface based on the selected neurostimulation program, and to receive a user command responding to the recommendation using the user interface.

In Example 2, the subject matter of Example 1 may optionally be configured such that the program selection circuit is configured to receive life factor information indicative of the environmental factor and the biopsychosocial factor.

In Example 3, the subject matter of Example 2 may optionally be configured such that the program selection circuit is configured to receive life factor information indicative of the environmental factor, the biopsychosocial factor, and a physical factor of the patient.

In Example 4, the subject matter of any one or any combination of Examples 1 to 3 may optionally be configured to further include an implantable system including the stimulation device and one or more sensors configured to sense one or more signals indicative of one or more of the environmental factor and the biopsychosocial factor of the patient.

In Example 5, the subject matter of Example 4 may optionally be configured such that the programing device comprises a smartphone.

In Example 6, the subject matter of any one or any combination of Examples 1 to 5 may optionally be configured such that the programing selection circuit includes a life factor input, a life factor metric generator, and a program selector. The life factor input is configured to receive the life factor information. The life factor metric generator is configured to generate one or more life factor metrics based on the received life factor information. The program selector is configured to select the neurostimulation program from the plurality of neurostimulation programs based on a relationship between the plurality of neurostimulation programs and the one or more life factor metrics.

In Example 7, the subject matter of Example 6 may optionally be configured such that the program selection circuit is configured to adjust the relationship for the patient based on a default relationship.

In Example 8, the subject matter of Example 7 may optionally be configured such that the relationship relates values or value ranges each specified for a life factor parameter in the one or more life factor metrics to a program of the plurality of neurostimulation programs, and the program selection circuit is configured to adjust the values or value ranges for the patient.

In Example 9, the subject matter of any one or any combination of Examples 6 to 8 may optionally be configured to further include one or more sensors configured to sense one or more signals and produce sensor information of the life factor information, and configured such that the life factor input includes a sensor input to receive the sensor information.

In Example 10, the subject matter of Example 9 may optionally be configured such that the one or more sensors include one or more environmental sensors including at least one of a pressure sensor to sense an atmospheric pressure, and a temperature sensor to sense an ambient temperature, a humidity sensor to sense a humidity, or a location sensor to identify the patient's instant location.

In Example 11, the subject matter of any one or any combination of Examples 9 and 10 may optionally be configured such that the one or more sensors include one or more biopsychosocial sensors configured to sense one or more biopsychosocial signals indicative of the patient's emotional state.

In Example 12, the subject matter of any one or any combination of Examples 9 to 11 may optionally be configured such that the life factor input further includes a patient input to receive patient information of the life factor information, the patent information including data obtained from the patient or the patient's medical record.

In Example 13, the subject matter of Example 12 may optionally be configured such that the patient input is configured to receive the patient's answers to questions related to the patient's emotional state.

In Example 14, the subject matter of any one or any combination of Examples 12 and 13 may optionally be configured such that the patient input is configured to receive the patient's demographics.

In Example 15, the subject matter of any one or any combination of Examples 9 to 14 may optionally be configured such that the life factor input further includes a media input to receive media information of the life factor information, the media information including data obtained from weather forecast.

An example (e.g., "Example 16") of a method for controlling delivery of neurostimulation from a stimulation device to a patient according to a selected neurostimulation program is also provided. The method may include communicating with the stimulation device using a programming device and selecting the neurostimulation program using the programing device. The selection may include receiving life factor information indicative of at least one of an environmental factor and a biopsychosocial factor of the patient, selecting the neurostimulation program from a plurality of neurostimulation programs based on the received life factor information, presenting a recommendation using a user interface of the programming device based on the selected neurostimulation program, and receiving a user command responding to the recommendation using the user interface.

In Example 17, the subject matter of Example 16 may optionally further include implementing the programming device in a smartphone.

In Example 18, the subject matter of selecting the neurostimulation program as found in any one or any combination of Examples 16 and 17 may optionally further include generating one or more life factor metrics based on the received life factor information and selecting the neurostimulation program from the plurality of neurostimulation programs based on a relationship between the plurality of neurostimulation programs and the one or more life factor metrics.

In Example 19, the subject matter of Example 18 may optionally further include establishing a default relationship using statistical information obtained using a patient population and establishing a custom relationship by adjusting the default relationship for the patient. The custom relationship is to be used for selecting the neurostimulation program from the plurality of neurostimulation programs for the patient.

In Example 20, the subject matter of receiving the life factor information as found in any one or any combination of Examples 16 to 19 may optionally further include receiving sensor information from one or more sensors configured to sense one or more signals indicative of the at least one of the weather at the patient's location or the emotional state of the patient.

In Example 21, the subject matter of receiving the sensor information from the one or more sensors as found Example 20 may optionally further include receiving biomarker information from a biomarker sensor configured to sense a signal indicative of a biomarker of at least one of the patient's emotional state.

In Example 22, the subject matter of receiving the life factor information as found in any one or any combination of Examples 16 to 21 may optionally further include receiving patient information from the patient or the patient's medical record. The patient information includes one or more of the patient's answers to questions related to the patient's emotional state.

In Example 23, the subject matter of receiving the life factor information as found in any one or any combination of Examples 16 to 21 may optionally further include receiving the life factor information further includes receiving media information of the life factor information. The media information is related to, or potentially related to, the at least one of the weather at the patient's location or the emotional state of the patient.

In Example 24, the subject matter of receiving media information as found in Example 23 may optionally further include receiving a weather forecast.

An Example "(e.g., "Example 25") of a non-transitory computer-readable storage medium is also provided. The non-transitory computer-readable storage medium includes instructions, which when executed by a system, may cause the system to perform a method for controlling delivery of neurostimulation from a stimulation device to a patient according to a selected neurostimulation program. The method may include communicating with the stimulation device using a programming device and selecting the neurostimulation program using the programing device. The selection may include receiving life factor information indicative of at least one of an environmental factor and a biopsychosocial factor of the patient, selecting the neurostimulation program from a plurality of neurostimulation programs based on the received life factor information, presenting a recommendation using a user interface of the programming device based on the selected neurostimulation program, and receiving a user command responding to the recommendation using the user interface.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
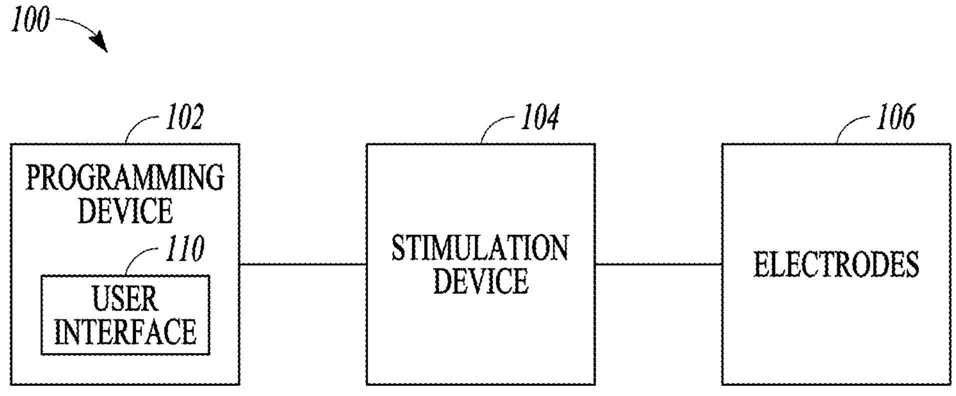
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized, and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system that can use patient life factors to control delivery of neurostimulation to the patient, such as by selecting a neurostimulation program based on the patient's biopsychosocial, environmental, and/or physical factors. In various embodiments, the neuromodulation system can include an implantable device configured to deliver neurostimulation (also referred to as neuromodulation) therapies, such as deep brain stimulation (DBS), spinal cord stimulation (SCS), peripheral nerve stimulation (PNS), and vagus nerve stimulation (VNS), and one or more external devices configured to program the implantable device for its operations and monitor the performance of the implantable device. While SCS is discussed as a specific example, the present subject matter can also be applied to program stimulation devices for delivering various types of neuromodulation therapies.

In an example of a current approach to therapy scheduling, neurostimulation programs are scheduled for delivery to a patient based on time (e.g., at certain hours of a day, certain days of a week, etc.). However, the patient's intrinsic and external conditions can change in a random and unpredictable manner. Such changes can affect the patient's responsiveness to some neurostimulation programs, thereby affecting the efficacy of the therapy. It has been learned that the patient life factors, such as the patient's emotional state, the weather at the patient's instant location, and the patient's weight and body mass index (BMI), can affect the efficacy of the therapy using certain neurostimulation programs.

The present subject matter uses patient life factors such as the biopsychosocial, environmental, and/or physical factors to select neurostimulation programs for the patient. Relationships each between a neurostimulation program and the patient life factors can be established to determine the performance of that neurostimulation program under a particular set of the patient's intrinsic and/or external conditions experienced during daily life. This allows neurostimulation programs to be mapped to the patient life factors and hence to be selected based on the patient life factors. In various embodiment, such life factors, including the patient's intrinsic and/or external conditions experienced during daily life, can be measured using various means including, but not limited to, sensors sensing signals from the patient, sensors sensing the patient's environmental conditions such as temperature and pressure, public information such as weather forecasts and reports, a tracking system identifying the patient's instant location, and input from the patient such as the patient's answers to various questions. Based on such measurements, a neurostimulation system according to the present subject matter can automatically select one or more neurostimulation programs for the patient and automatically apply the selected program(s) or present the selected program(s) as a recommendation for the patient or a caregiver to decide whether to apply.

In this document, a "patient" includes a person receiving treatment delivered using a neurostimulation system according to the present subject matter, a "user" includes a physician or other caregiver who treats the patient using the neurostimulation system, and a "patent life factor" (or "life factor") includes an intrinsic or external condition experienced by the patient during his/her daily life. Examples of the patient life factors include, but are not limited to, the patient's biopsychosocial, environmental, and physical factors (with more specific examples for each of these factors discussed below). While biopsychosocial, environmental, and physical factors are specifically discussed as examples, the present subject matter can be applied to use any one or more of the patient life factors to control delivery of neurostimulation.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust his or her treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
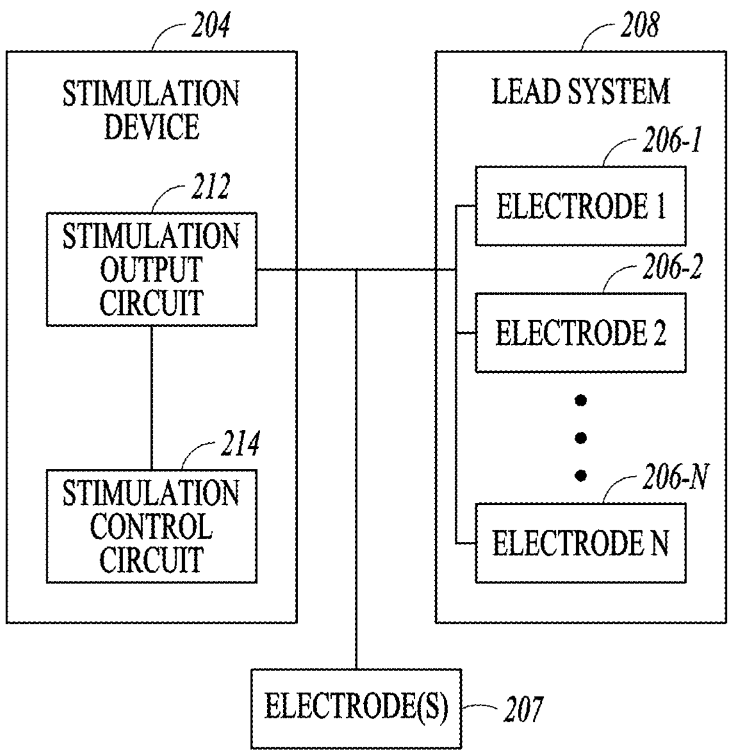
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an example of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
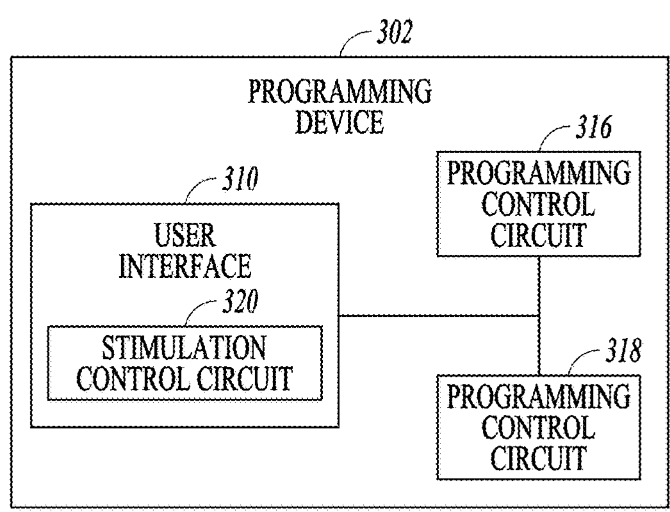
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an example of programming device 102 and includes a storage device 318, a programming control circuit 316, and a user interface 310. Programming control circuit 316 generates the plurality of stimulation parameters that controls the delivery of the neurostimulation pulses according to a specified neurostimulation program that can define, for example, stimulation waveform and electrode configuration. User interface 310 represents an example of user interface 110 and includes a stimulation control circuit 320. Storage device 318 stores information used by programming control circuit 316 and stimulation control circuit 320, such as information about a stimulation device that relates the neurostimulation program to the plurality of stimulation parameters. In various embodiments, stimulation control circuit 320 can be configured to support one or more functions allowing for programming of stimulation devices, such as stimulation device 104 including its various embodiments as discussed in this document, according to one or more selected neurostimulation programs as discussed in this document.

In various embodiments, user interface 310 can allow for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. As used in this document, a "neurostimulation program" can include the pattern of neurostimulation pulses including the one or more stimulation fields, or at least various aspects or parameters of the pattern of neurostimulation pulses including the one or more stimulation fields. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and stimulation control circuit 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
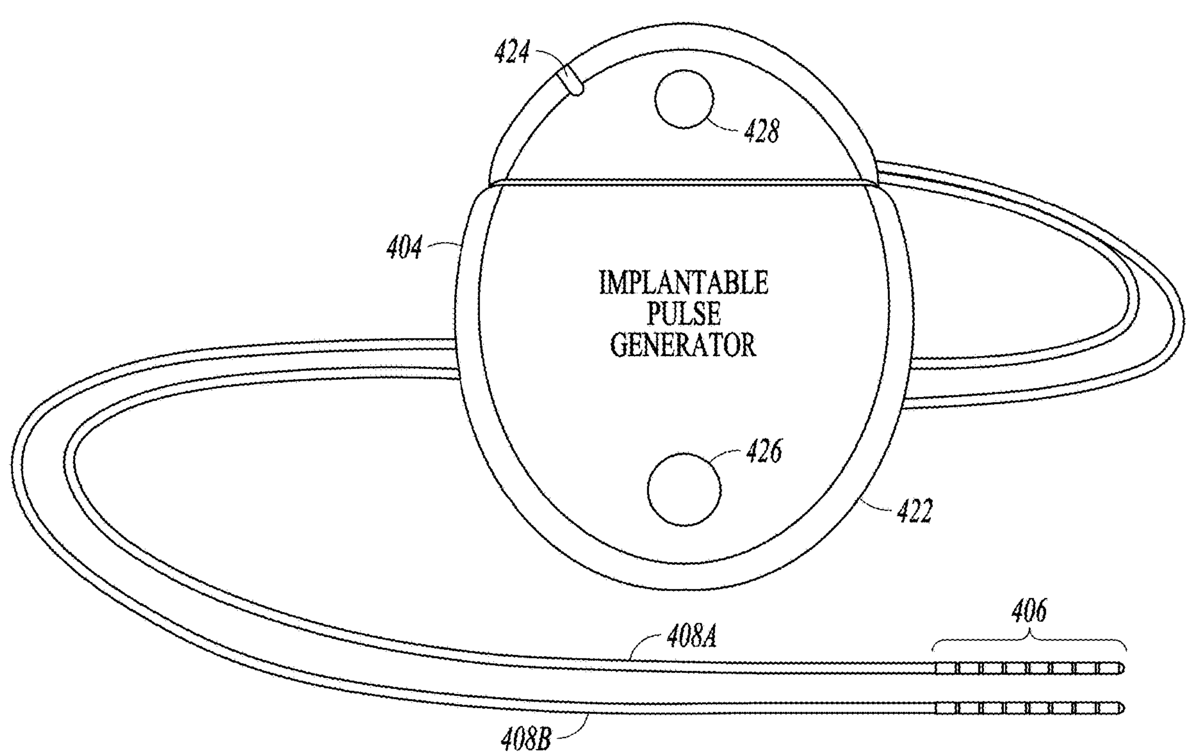
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain or configured to provide electrical neurostimulation energy to a nerve cell target included in the subject's spinal cord.

Figure 5:
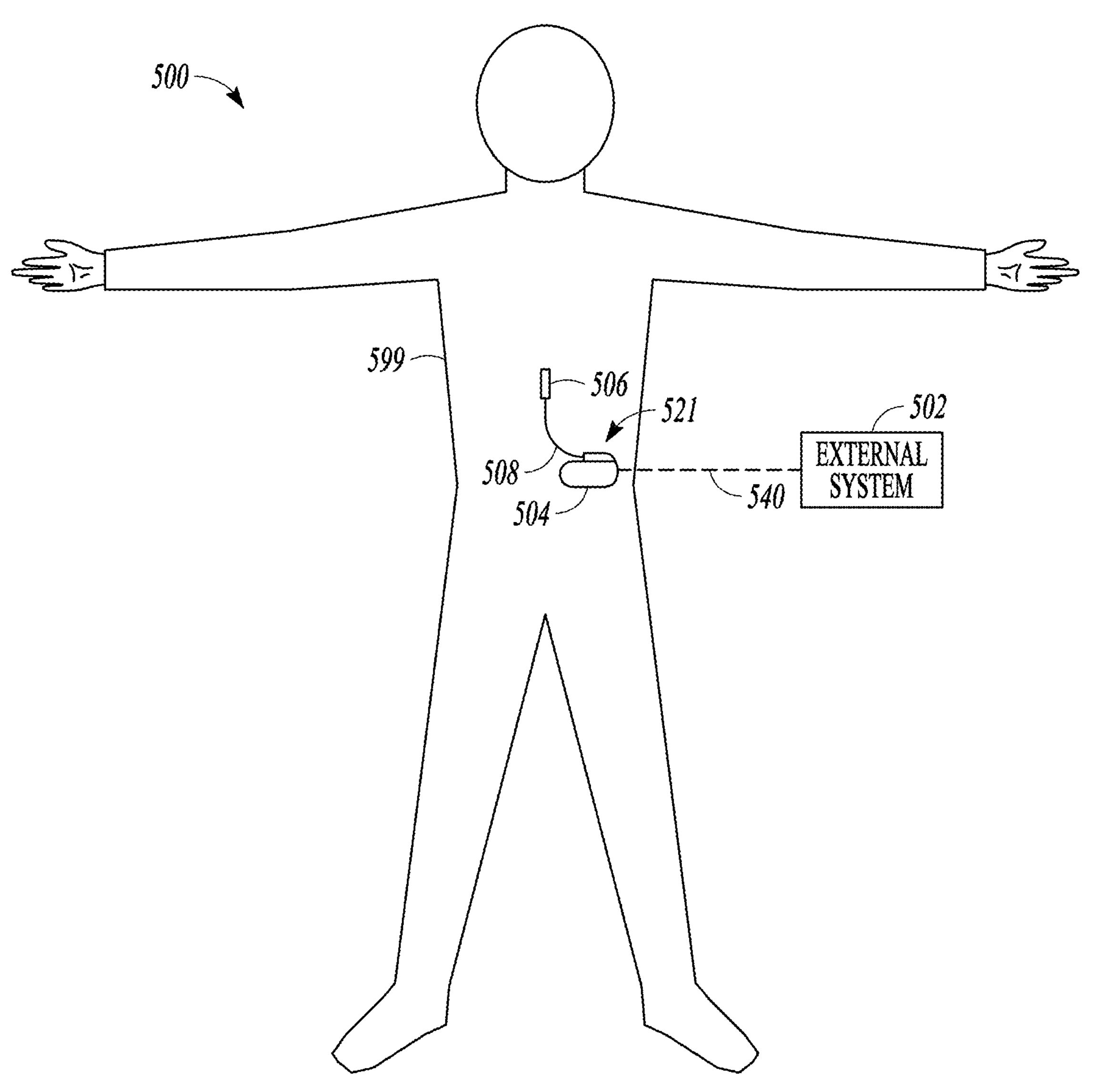
FIG. 5 illustrates an embodiment of an IPG and an implantable lead system, such as the IPG and lead system of FIG. 4, arranged to provide neurostimulation to a patient.

FIG. 5 illustrates an implantable neurostimulation system 500 and portions of an environment in which system 500 may be used. System 500 includes an implantable system 521, an external system 502, and a telemetry link 540 providing for wireless communication between implantable system 521 and external system 502. Implantable system 521 is illustrated in FIG. 5 as being implanted in the patient's body 599.

Implantable system 521 includes an implantable stimulator (also referred to as an implantable pulse generator, or IPG) 504, a lead system 508, and electrodes 506, which represent an example of stimulation device 204, lead system 208, and electrodes 206, respectively. External system 502 represents an example of programming device 302. In various embodiments, external system 502 includes one or more external (non-implantable) devices each allowing the user and/or the patient to communicate with implantable system 521. In some embodiments, external 502 includes a programming device intended for the user to initialize and adjust settings for implantable stimulator 504 and a remote control device intended for use by the patient. For example, the remote control device may allow the patient to turn implantable stimulator 504 on and off and/or adjust certain patient-programmable parameters of the plurality of stimulation parameters.

The sizes and sharps of the elements of implantable system 521 and their location in body 599 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regarding less of stimulation targets in the patient's body and whether the stimulation device is implantable.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
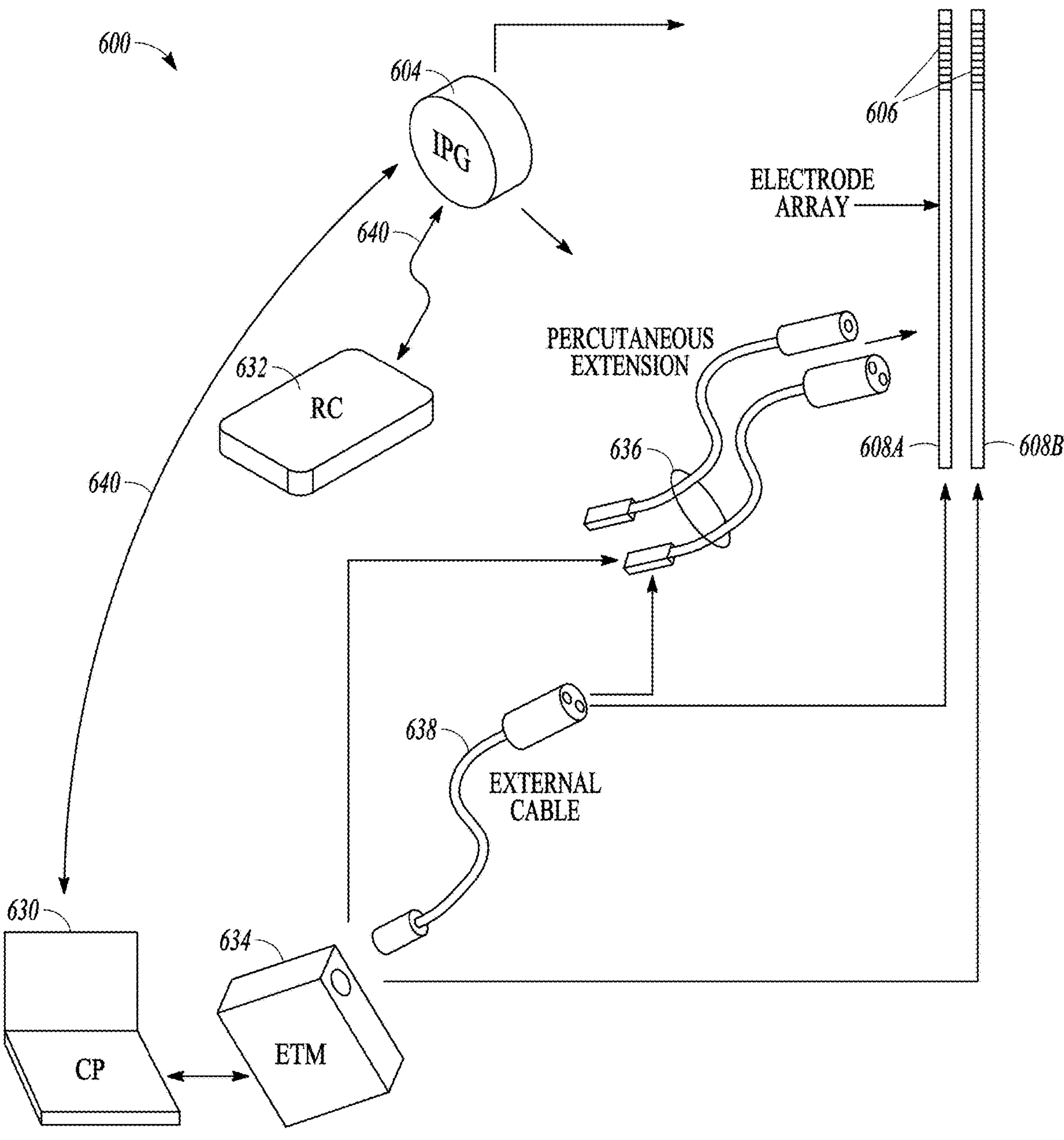
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 represents an example of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630. CP 630 may communicate with ETM 634 using a wired connection (e.g., over a USB link) or by wireless telemetry using a wireless communications link 640. CP 630 also communicates with IPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a preprogrammed stimulation pulse train is applied. RC 632 may be programmed by CP 630. CP 630 may communicate with the RC 632 using a wired or wireless communications link. In some embodiments, CP 630 can program RC 632 when remotely located from RC 632.

Figure 7:
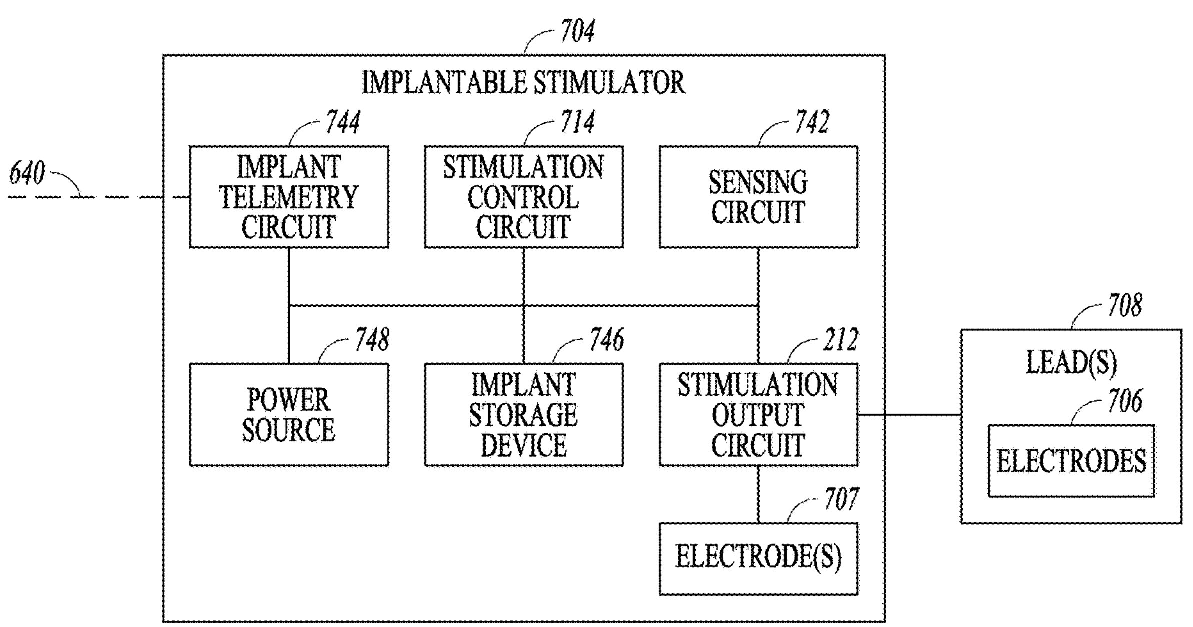
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an example of stimulation device 104 or 204 and may be implemented, for example, as IPG 604. Lead(s) 708 represents an example of lead system 208 and may be implemented, for example, as implantable leads 608A and 608B. Lead(s) 708 includes electrodes 706, which represents an example of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707 and delivers each of the neurostimulation pulses through a set of electrodes selected from electrodes 706 and electrode(s) 707. Stimulation control circuit 714 represents an example of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 can store one or more neurostimulation programs and values of the plurality of stimulation parameters for each of the one or more neurostimulation programs. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640 and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of post-operative lead placement to magnetic resonance imaging (MRI) of the brain), clinical effect map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
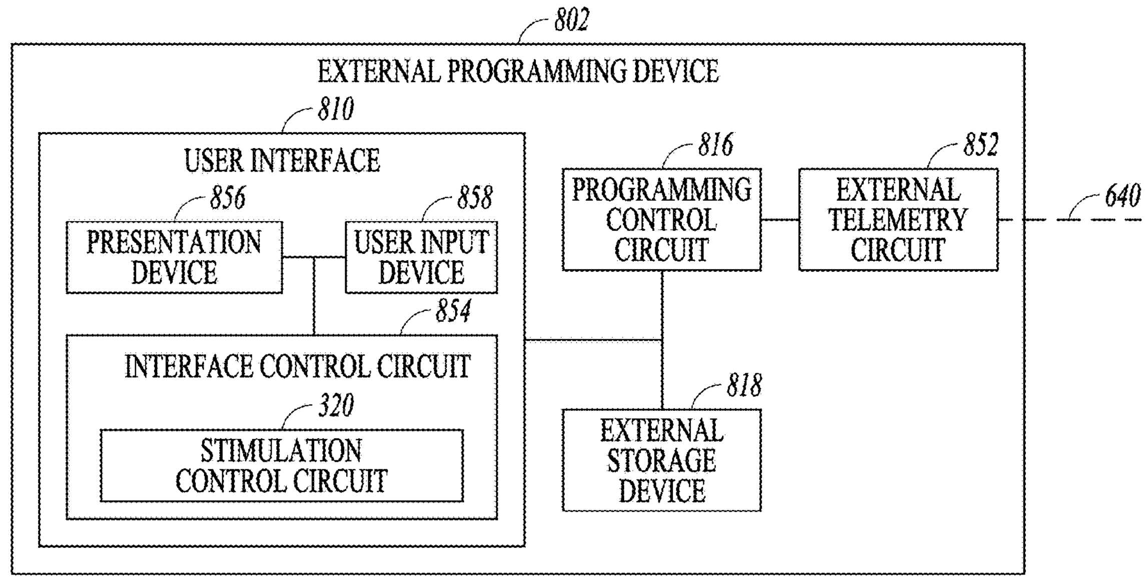
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an example of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. Such definition of the current distribution may be referred to as "fractionalization" in this document. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an example of programming control circuit 316 and generates the plurality of stimulation parameters, which is to be transmitted to implantable stimulator 704, based on a specified neurostimulation program (e.g., the pattern of neurostimulation pulses as represented by one or more stimulation waveforms and one or more stimulation fields, or at least certain aspects of the pattern). The neurostimulation program may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an example of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI. The GUI may also allow the user to perform any functions discussed in this document where graphical presentation and/or editing are suitable as may be appreciated by those skilled in the art.

Interface control circuit 854 controls the operation of user interface 810 including responding to various inputs received by user input device 858 and defining the one or more stimulation waveforms. Interface control circuit 854 includes stimulation control circuit 320.

In various embodiments, external programming device 802 can have operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms and transmits the plurality of stimulation parameters with the updated values to implantable stimulator 704.

Figure 9:
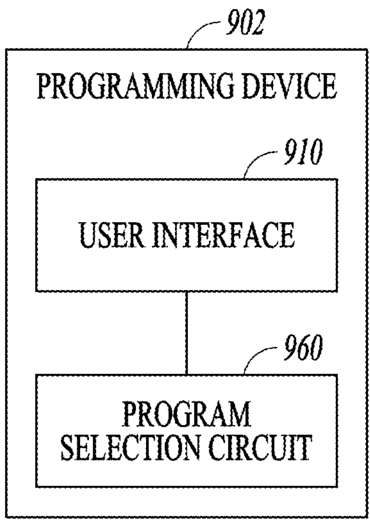
FIG. 9 illustrates an embodiment of a programming device including a program selection circuit.

FIG. 9 illustrates an embodiment of a programming device 902. Programming device 902 represents an example of programming device 102, 302, or 802 of portions thereof, and may be implemented, for example, as CP 630 and/or RC 632 of portions thereof. In various embodiments, programming device 902 can be used to communicate with a stimulation device that can be configured to deliver neurostimulation and to control the delivery of the neurostimulation according to a selected neurostimulation program and can be used to select the neurostimulation program. While "a selected neurostimulation program" is used as an example for discussion rather than limiting the selection and subsequent delivery to a single neurostimulation program. In various embodiments, a single neurostimulation program can be selected for delivery, or multiple neurostimulation programs can be selected for simultaneous, concurrent, or sequential delivery, by applying the present subject matter for the selection. Thus, the "selected neurostimulation program" as used in this document can include the single neurostimulation program or the multiple neurostimulation programs selected according to the present subject matter.

Programming device 902 can include a user interface 910 and a program selection circuit 960. An example of user interface 910 can include user interface 810. Program selection circuit 960 can receive life factor information indicative of patient life factors including environmental, biopsychosocial, and physical factors of the patient and select the neurostimulation program from a plurality of neurostimulation programs based on the received life factor information. In various embodiments, program selection circuit can present a recommendation using the user interface based on the selected neurostimulation program and receive a user command responding to the recommendation using the user interface.

In various embodiments, programming device 902 can be a hand-held device provided to the patient to communicate with the stimulation device directly or via another programming device (e.g., RC 632). In various embodiments, programming device 902 can be implemented as a stand-alone device or a component of the system that also includes another one or more programming devices (e.g., as CP 630 and/or RC 632). In various embodiments, programming device 902 can be implemented as a dedicated device configured to provide at least selected structures and functions of the one or more programming devices, or it can be implemented by adding functionality to an existing device. For example, programming device 902 can be implemented by installing an application software in a smartphone that can communicate with the stimulation device directly or another programing device such as RC 632, or it can be implemented by adding functions of program selection circuit 960 to RC 632.

Figure 10:
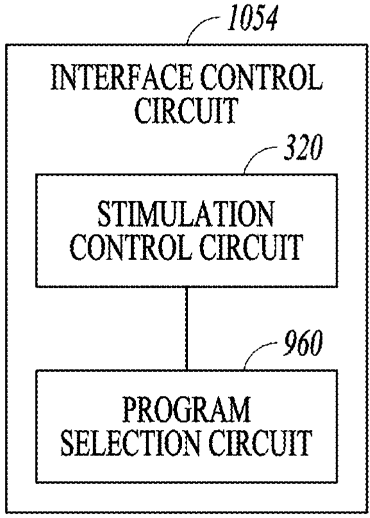
FIG. 10 illustrates an embodiment of an interface control circuit as part of an external programming device, such as the external programming device of FIG. 8.

FIG. 10 illustrates an embodiment of an interface control circuit 1054, which represents an example of interface control circuit 854. The illustrated embodiment represents an example in which programming device 902 is implemented as part of external programming device 802.

Interface control circuit can include stimulation control circuit 320 and program selection circuit 960. Program selection circuit 960 can select the neurostimulation program, and stimulation control circuit 320 can generate the stimulation parameters for programing the stimulation device to deliver neurostimulation and to control the delivery of the neurostimulation according to the selected neurostimulation program. In various embodiments, program selection circuit 960 can present information related to the selection of the neurostimulation program using presentation device 856 and can receive one or more user commands related to the selection of the neurostimulation program using user input device 858.

Figure 11:
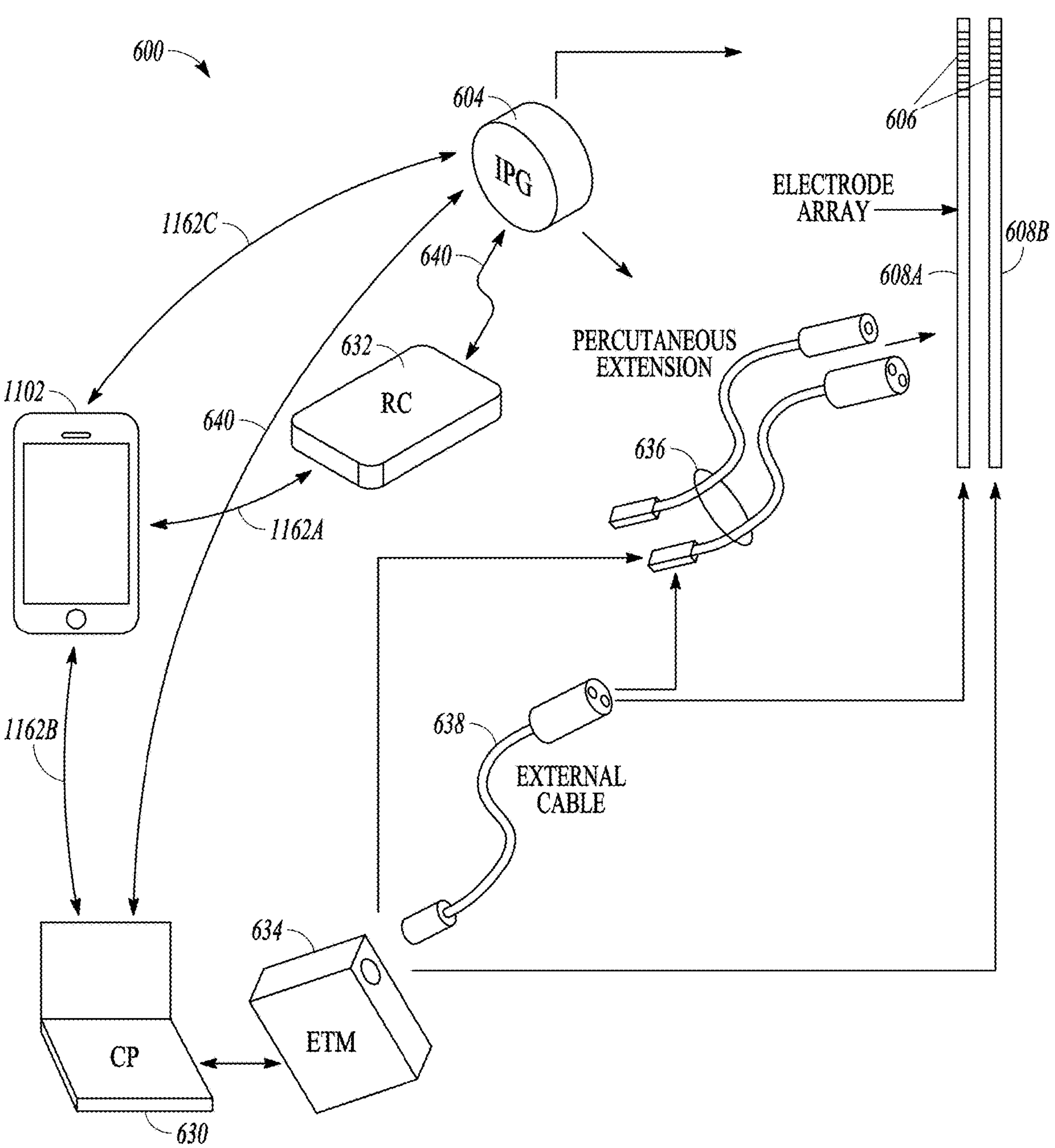
FIG. 11 illustrates an embodiment of the programming device configured to be communicatively coupled to an implantable neurostimulation system, such as the implantable neurostimulation system of FIG. 6.

FIG. 11 illustrates an embodiment of a programming device 1102 configured to be communicatively coupled to an implantable neurostimulation system, such as system 600 as shown in FIG. 11 by way of example, but not by way of restriction. Programming device 1102 represents an example of programing device 902 as implemented in a hand-held device that can communicate with the stimulation device directly or via another programming device. In various embodiments, programming device 1102 can be a generic device including application software installed to provide at least selected structures and functions of the one or more programming devices. Examples of the generic device include a smartphone, a laptop computer, or a tablet computer. The selected structures and functions can include the structures and functions not provided by another one or more programming devices of the system that functions with programming device 1102.

In the illustrated embodiment, programming device 1102 can communicate with RC 632 via wireless communications link 1162A, communicate with CP 630 via wireless communications link 1162B, and communicate with IPG 604 via wireless communications link 1162C. In various embodiments, programming device 1102 can communicate with RC 632 via wireless communications link 1162A, communicate with CP 630 via wireless communications link 1162B, and/or communicate with IPG 604 via wireless communications link 1162C. This allows programming device 1102 to communicate with the stimulation device (e.g., IPG 604) directly or via another programming device (e.g., RC 632 or CP 630).

Figure 12:
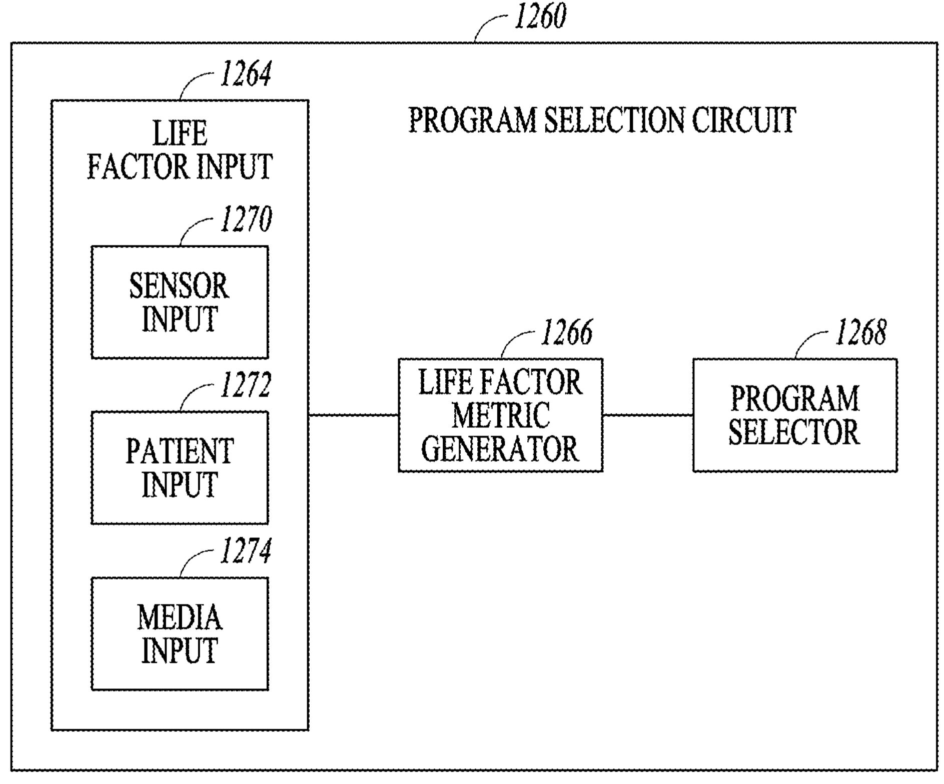
FIG. 12 illustrates an embodiment of the program selection circuit.
Figure 13:
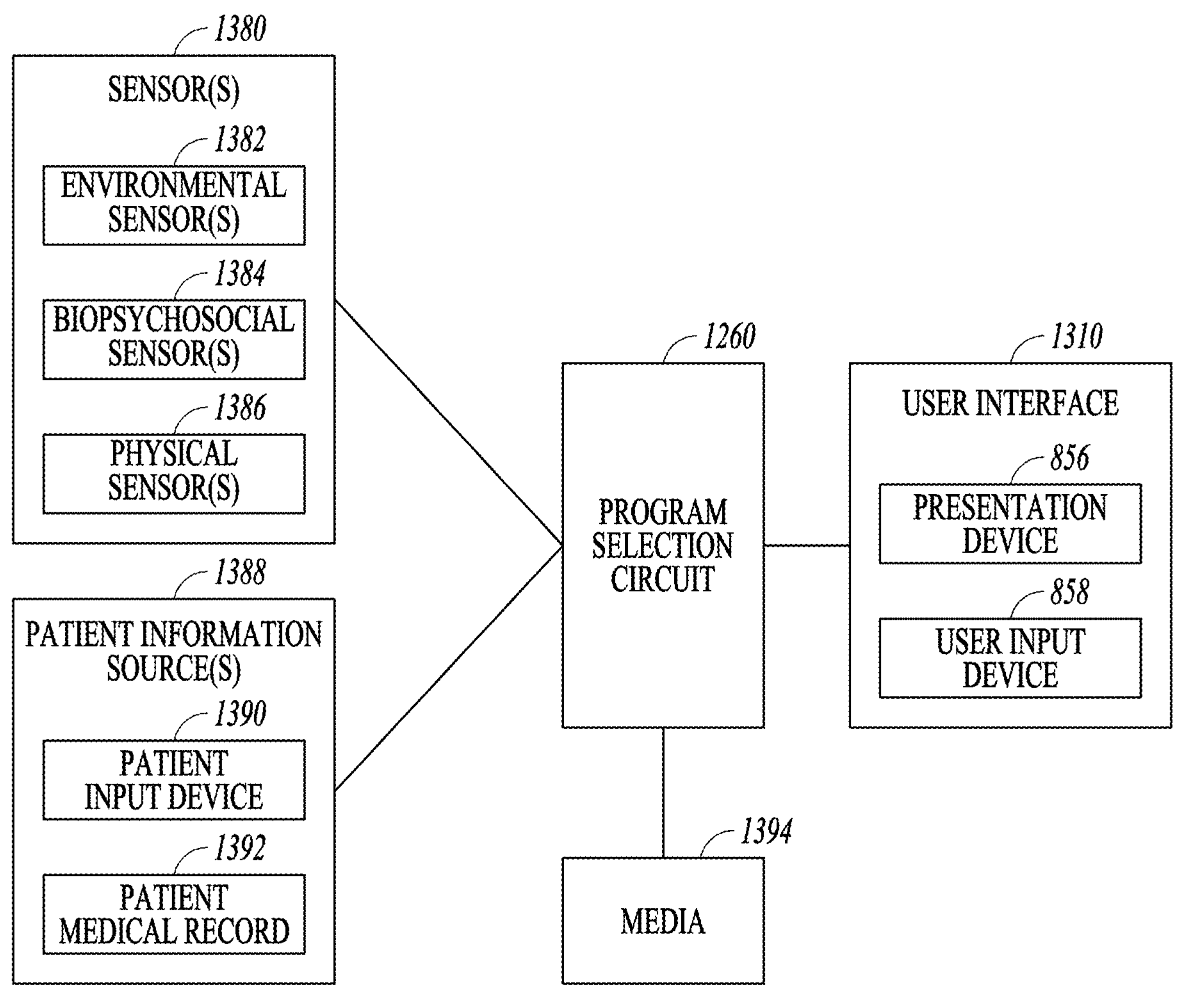
FIG. 13 illustrates an embodiment of the program selection circuit with various input devices from which the program selection circuit receives information and a user interface allowing for user access to the program selection circuit.

FIG. 12 illustrates an embodiment of a program selection circuit 1260. Program selection circuit 1260 represents an example of program selection circuit 960 and can include a life factor input 1264, a life factor metric generator 1266, and a program selector 1268. FIG. 13 illustrates an embodiment of program selection circuit 1260 with various input devices from which program selection circuit 1260 receives information and a user interface 1310 allowing for user access to program selection circuit 1260.

Life factor input 1263 can receive life factor information indicative of one or more patient life factors. Examples of the one or more life factors include environmental factors, biopsychosocial factors, and/or physical factors. Environmental factors can include indicators of the environment at the patient's instant location and/or residential location, such as weather at the patient's instant location and climate of the patient's residential location. Biopsychosocial factors can include the patient's cognition, emotional state (mood), and/or personality traits (that can predispose certain emotional states). Physical factors can include the patient's weight and/or body mass index (BMI). In various embodiments, the one or more patient life factors are selected from various factors that may affect the patient's condition being treated by the neurostimulation and/or the efficacy of the neurostimulation. In various embodiments, the one or more patient life factors are used to adjust the neurostimulation in addition to monitoring the patient's condition being treated by the neurostimulation.

In the illustrated embodiment, life factor input 1264 includes a sensor input 1270, a patient input 1272, and a media input 1274. In various embodiments, life factor input 1264 can include sensor input 1270, patient input 1272, and/or media input 1274. Sources of the information received by life factor input 1264, as illustrated in FIG. 13, can include one or more sensors 1380, one or more patient information sources 1388, and media 1394.

Sensor input 1270 can receive sensor information of the life factor information. The sensor information can include data acquired using sensor(s) 1380, which produce one or more sensor signals to be received by sensor input 1270. As illustrated in FIG. 13, examples of sensor(s) 1380 include one or more environmental sensors 1382, one more biopsychosocial sensors 1384, and/or one more physical sensors 1386. Environmental sensor(s) 1382 can sense one or more environmental signals indicative of the environmental factors. Examples of environmental sensor(s) 1382 include a pressure sensor to sense an atmospheric pressure (also referred to as barometric pressure, numerical value in Pascal, mmHg, inHg, or psi), a temperature sensor (thermometer) to sense an ambient temperature (numerical value in degrees Celsius or Fahrenheit), a humidity sensor to sense a humidity (relative humidity: numerical value in percentage; absolute humidity: numerical value in grams of water vapor per cubic meter of air, $g/m^3$), and/or a location sensor to identify the patient's instant location (such as a global positioning system). Biopsychosocial sensor(s) 1384 can sense one or more biopsychosocial signals indicative of the biopsychosocial factors (e.g., stress and/or mood biomarkers). Examples of biopsychosocial sensor(s) 1384 include a facial recognition sensor to sense the patient's facial expression, a voice sensor (e.g., microphone) to sense the patient's voice, a sleep sensor to sense the patient's sleep state (e.g., for detecting lack of sleep), a heart rate sensor to sense the patient's heart rate, a blood pressure sensor to sense the patient's blood pressure, an electrodermal activity (EDA) sensor to sense the patient's EDA (e.g., galvanic skin response), and/or an electrochemical sensor to sense stress biomarkers from the patient's body fluids (e.g., enzymes and/or ions, such as lactate or cortisol from saliva or sweat). Physical sensor(s) 1386 can sense one or more physical signals indicative of the physical factors. Examples of physical sensor(s) 1386 include a weight scale and/or a body composition analyzer.

Patient input 1272 can receive patient information of the life factor information. The patent information can include data obtained from patient information source(s) 1388. As illustrated in FIG. 13, patient information source(s) 1388 includes a patient input device 1390, which allows for the data to be received from the patient directly, and a patient medical record 1392, which stores the patient information obtained at various times. Examples of the patient information include the patient's answers to a questionnaire (in which questions can in forms of text, drawings, and/or small tasks designed to obtain answers), the patient's self-rating of emotional state, the patient's selection of the patient's emotional state from a list of predefined emotional states (e.g., happy, sad, depressed, anxious, and angry), the patient's demographics (e.g., gender, age, residence location, current location, and other information related to patient's perception of being cold or warm, climate-related seasonal depression, tolerance to pain, responsiveness to neurostimulation, etc.), the patient's weight and BMI, and the patient's personality trait.

Media input 1394 can receive media information of the life factor information. The media information can include data obtained from media 1392, which can represent any one or any combination of various media resources such as radio broadcasting, publications, social media, and the Internet. Examples of the media information include weather forecast (e.g., including atmospheric pressure; ambient temperature; humidity; weather state such as sunshine, cloud, wind, lightning, storm, hurricane, tornado, rain, hail, and snow), environmental reporting, news reporting that may affect the patient's emotional state, and social network information indicative of the patient's emotional state (e.g., social media detecting depression from the patient's voices and/or writings).

In various embodiments, some types of the life factor information can be obtained by more than one way. For example, the patient's instant location can be provided by the location sensor or manually entered by the patient, and ambient temperature can be obtained from radio weather reporting or sensed by a thermometer. Which one or more specific patient life factors are obtained and used in each application of the present subject matter can depend on availability of information resources, capability of the programming device, and other design considerations as understood by those skilled in the art upon reading this document.

Referring to FIG. 12, life factor metric generator 1266 can generate one or more life factor metrics based on the received life factor information. In one embodiment, life factor metric generator 1266 generates a single life factor metric represents a measure of one or more patient life factors used in the selection of the neurostimulation program. In another embodiment, life factor metric generator 1266 generates a plurality of life factor metrics each being a measure of a life factor of a plurality of patient life factors used in the selection of the neurostimulation program. Each life factor metric can include one or more life factor parameters extracted from the received life factor information. In various embodiments, the single life factor metric and the plurality of life factor metrics can include one or more metrics selected from an environmental metric, a biopsychosocial metric, and a physical metric. The environmental metric can include one or more environmental parameters such as selected from parameters detected from the one or more environmental signals to indicate atmospheric pressure, ambient temperature, humidity, and location, parameters detected from the patient information to indicate the instant and/or residential locations, parameters detected from the media information to indicate atmospheric pressure, ambient temperature, humidity, location, weather state, or any other information available from weather forecast or reporting. The biopsychosocial metric can include one or more biopsychosocial parameters such as selected from parameters detected from the one or more biopsychosocial signals to indicate facial expression, voice, heart rate, blood pressure, EDA, and stress biomarkers, parameter detected from the patient information to indicate the patient's answers related to the patient's emotional state and personality traits, parameters detected from the media information to indicate events that may affect the patient's emotional state and the patient's emotional state as detected by the social media. The physical metric can include one or more physical parameters such as selected from parameters detected from the one or more physical signals to indicate weight and body composition and parameters detected from the patient information such as the weight and BMI.

Program selector 1268 can select the neurostimulation program from the plurality of neurostimulation programs based on a relationship between the plurality of neurostimulation programs and the one or more life factor metrics generated by the life factor metric generator 1266. In various embodiments, the plurality of neurostimulation programs can include neurostimulation programs with one or more parameters specified for certain ranges of a life factor parameter. For example, if a patient is known to be less responsive to neurostimulation during winter, the one or more parameters may be set to increase the intensity (e.g., amplitude and/or width of neurostimulation pulses) and/or dosage (e.g., duration and/or duty cycle for a neurostimulation therapy session) of the neurostimulation when the ambient temperature is below a certain threshold. Likewise, if a patient is known to be less responsive to neurostimulation when feeling depressed, the one or more parameters may be set to increase the intensity (e.g., amplitude and/or width of neurostimulation pulses) and/or dosage (e.g., duration and/or duty cycle of a neurostimulation therapy session) of the neurostimulation when the patient's emotional state indicates depression. In one embodiment, the type(s) of life factors used by program selector 1268 is programmable. The selection can be programmed to be based on one or more metrics selected from the environmental metric, the biopsychosocial metric, and the physical metric, for example through user interface 1310. This allows the patient to try and choose therapeutic options. For example, a particular patient may find weather has a significant impact on his response to the neurostimulation while his emotional state has little impact and may want to choose his selection of neurostimulation program to be based on the environmental and physical metrics only.

The relationship between the plurality of neurostimulation programs and the one or more life factor metrics can be empirically determined. For example, a default relationship can be empirically determined for a patient population, and a custom relationship determined for the patient by adjusting the default relationship for the patient. In various embodiments, program selection circuit 1260 can be used to experiment and customize various neurostimulation programs for an individual patient, and results used to determine the relationship for this patient. In various embodiments, the relationship can relate values or values ranges each specified for a life factor parameter in the one or more life factor metrics to a program of the plurality of neurostimulation programs. The default relationship can be determined by using statistical data obtained from the patient population to define these values or value ranges, and the custom relationship can be determined by fine-tuning these values or value ranges for each individual patient.

Referring to FIG. 13, the user interface 1310 represents an example of user interface 910, and can be identical or substantially similar to user interface 810, including presentation device 856 and user input device 858 as discussed above with reference to FIG. 8. In one embodiment, program selection circuit 1260 presents a recommendation to the patient using presentation device 856 based on the selected neurostimulation program, receive a user command accepting the recommendation using user input device 858, and communicate with the stimulation device for delivering the neurostimulation according to the selected neurostimulation program in response to the user command. This allows the patient to participate in the program selection based on his past experience with various neurostimulation programs, his actual emotional state, and/or his feeling about switching programs. In another embodiment, program selection circuit 1260 applies the selected neurostimulation program without checking with the patient. In another embodiment, program selection circuit 1260 can programed for applying the selected neurostimulation program either after checking with the patient and receiving the acceptance command or without checking with the patient, for example based on the patient's preference.

Figure 14:
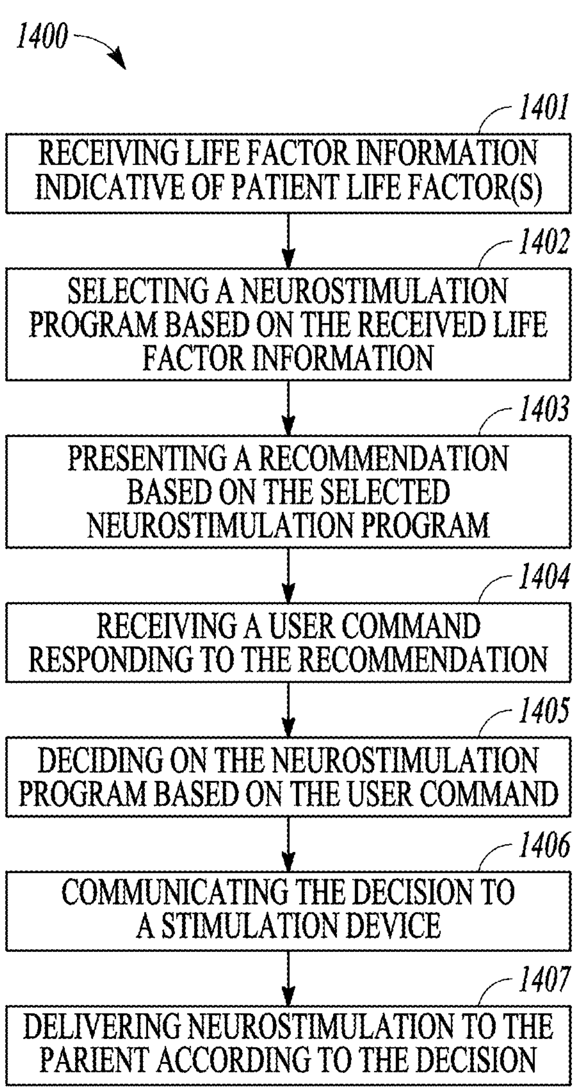
FIG. 14 illustrates an embodiment of a method for controlling delivery of neurostimulation from a stimulation device to a patient according to a selected neurostimulation program.

FIG. 14 illustrates an embodiment of a method 1400 for using a programming device to control delivery of neurostimulation from a stimulation device to a patient according to a selected neurostimulation program. Examples of the stimulation device include stimulation device 104 and its various embodiments (e.g., 204, 404, 504, 604, and 704) as discussed in this document. Programming device 902, including the various embodiments of its elements as discussed in this document, can be configured to be the programming device for performing method 1400. Method 1400 can be performed, but is not limited to being performed, using system 100, including its various embodiments of its elements as discussed in this document.

At 1401, life factor information indicative of one or more patient life factors is received. The one or more life factors can include environmental, biopsychosocial, and/or physical factors of the patient. In one embodiment, the received life factor information is indicative of environmental, biopsychosocial, and physical factors of the patient. In other embodiments, the received life factor information is indicative of any subset of one or two of the environmental, biopsychosocial, and physical factors of the patient. The lift factor information can be received from one or more resources including, but not limited to, one or more sensors (e.g., sensors sensing from the patient and/or the environment of the patient), the patient (e.g., a device receiving input from the patient and/or a caregiver attending the patient, and/or the patient's medical record), and/or the media (e.g., weather and news reporting including environmental information and information that may affect the patient's emotional state).

At 1402, a neurostimulation program is selected based on the received life factor information. In various embodiments, the neurostimulation program is selected from a plurality of neurostimulation programs that is stored in the stimulation device and/or the programming device. The selection process can include generating one or more life factor metrics based on the received life factor information and selecting the neurostimulation program from the plurality of neurostimulation programs based on a relationship between the plurality of neurostimulation programs and the one or more life factor metrics. In various embodiments, a default relationship is established using statistical information obtained using a patient population. In various further embodiments, a custom relationship is established by adjusting the default relationship for the patient. The custom relationship can be used for selecting the neurostimulation program from the plurality of neurostimulation programs stored for the patient. One or more neurostimulation programs of the plurality of neurostimulation programs stored for the patient can be adjusted when deemed necessary during the process of establishing the custom relationship.

At 1403, a recommendation is presented using a user interface of the programming device based on the selected neurostimulation program. In various embodiments, the user interface may display information identifying the selected neurostimulation program and optionally one or more reasons for the selection, in terms suitable for understanding by the patient. In various embodiments, the patient is allowed to decide on whether to accept the recommendation. In other embodiments, a decision to apply the selected neurostimulation program is to be made without checking with the patient, and the performance of method 1400 continues from step 1406 (skipping steps 1404 and 1405).

At 1404, a user command responding to the recommendation is received using the user interface. At 1405, a decision on selecting a neurostimulation program based on the user command is made. In various embodiments, if the recommendation is not accepted as indicated by the user command, the received life factor information does not change the delivery of the neurostimulation as originally scheduled. For example, the stimulation device is programmed to deliver a sequence of one or more neurostimulation programs according to an original or default schedule. The recommendation relates to whether a scheduled delivery for a neurostimulation program should be modified by switching to a different neurostimulation program based on the received life factor information. In various other embodiments, if the recommendation is not accepted as indicated by the user command, selection of another neurostimulation program can be recommended based on a predetermined selection process. At 1406, if the recommendation is accepted as indicated by the user command, or if the patient is not to participate in the decision process, the decision to apply the selected neurostimulation program is communicated to the stimulation device. In various embodiments, this affects only the next neurostimulation program scheduled to be delivered from the stimulation device. In one embodiment, if the recommendation has been presented for a specified time interval without receiving a response, the decision to apply the selected neurostimulation program is made and communicated to the stimulation device. In another embodiment, if the recommendation has been presented for a specified time interval without receiving a response, no change to the delivery of the neurostimulation as originally scheduled is to be made.

At 1407, the neurostimulation is delivered to the patient according to the decision. In various embodiments, the decision on whether to apply the neurostimulation program selected based on the received life factor information affects only the neurostimulation program that is next in the line for delivery from the stimulation device according to the original or default schedule. In various embodiments, the programming device can be configured for performing method 1400 immediately (e.g., within 5 minutes) before a scheduled delivery of the neurostimulation to decide which neurostimulation program should be applied based on the received life factor information.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for delivering neurostimulation from a stimulation device to a patient, comprising:

storing a plurality of neurostimulation programs in a programming device configured for use by the patient, the neurostimulation programs each defining a pattern of neurostimulation pulses using a set of stimulation waveforms and stimulation fields;

receiving at least one of environmental information or biopsychosocial information of the patient using the programming device; and controlling the delivery of the neurostimulation using the programing device, including:

selecting a neurostimulation program from the stored plurality of neurostimulation programs based on the received at least one of the environmental information or the biopsychosocial information of the patient;

presenting a recommendation for applying the selected neurostimulation program using a user interface of the programming device;

waiting to receive a user command responding to the presented recommendation using the user interface, and communicating to the stimulation device to deliver the neurostimulation according to the selected neurostimulation program in response to the recommendation being presented for a specified time interval without receiving the user command.

2. The method of claim 1, comprising receiving the environmental information and selecting the neurostimulation program from the stored plurality of neurostimulation programs based on the received environmental information.

3. The method of claim 2, wherein receiving the environmental information comprises receiving indicators of environment at the patient's instant location and residential location.

4. The method of claim 1, comprising receiving the biopsychosocial information and selecting the neurostimulation program from the stored plurality of neurostimulation programs based on the received biopsychosocial information.

5. The method of claim 4, further comprising sensing one or more biopsychosocial signals indicative of the biopsychosocial information using one or more sensors.

6. The method of claim 5, wherein sensing the one or more biopsychosocial signals comprises sensing the patient's facial expression.

7. The method of claim 5, wherein sensing the one or more biopsychosocial signals comprises sensing the patient's voice.

8. The method of claim 5, wherein sensing the one or more biopsychosocial signals comprises sensing the patient's sleep state.

9. The method of claim 5, wherein sensing the one or more biopsychosocial signals comprises sensing the patient's electrodermal activity.

10. The method of claim 5, wherein sensing the one or more biopsychosocial signals comprises sensing stress biomarkers from the patient's body fluids.

11. The method of claim 1, further comprising receiving media information from media resources using the programming device and selecting the neurostimulation program from the stored plurality of neurostimulation programs based on the received media information.

12. The method of claim 11, wherein receiving the media information from the media resources comprises receiving social network information indicative of the patient's emotional state from social media.

13. A system for delivering neurostimulation to a patient, comprising:

a stimulation device configured to deliver the neurostimulation according to a selected neurostimulation program; and a programming device configured for use by the patient to communicate with the stimulation device, the programing device including:

a storage device configured to store a plurality of neurostimulation programs each defining a pattern of neurostimulation pulses using a set of stimulation waveforms and stimulation fields;

a user interface; and a program selection circuit configured to receive at least one of environmental information or biopsychosocial information of the patient, to select the neurostimulation program from the stored plurality of neurostimulation programs based on the received at least one of the environmental information or the biopsychosocial information of the patient, to present a recommendation for applying the selected neurostimulation program using the user interface, to receive a user command responding to the presented recommendation using the user interface, and to communicate to the stimulation device to deliver the neurostimulation according to the selected neurostimulation program in response to the recommendation being presented for a specified time interval without receiving the user command.

14. The system of claim 13, wherein the programing device comprises a smartphone.

15. The system of claim 13, wherein the program selection circuit is configured to receive the environmental information and to select the neurostimulation program from the stored plurality of neurostimulation programs based on the received environmental information.

16. The system of claim 13, wherein the program selection circuit is configured to receive the biopsychosocial information and to select the neurostimulation program from the stored plurality of neurostimulation programs based on the received biopsychosocial information.

17. The system of claim 16, further comprising one or more sensors configured to sense one or more biopsychosocial signals indicative of the biopsychosocial information.

18. The system of claim 13, wherein the storage device is configured to store a relationship between the stored plurality of neurostimulation programs and one or more metrics, and the programing selection circuit is configured to generate the one or more metrics based on the received at least one of the environmental information or the biopsychosocial information of the patient and to select the neurostimulation program from the stored plurality of neurostimulation programs using the stored relationship and the generated one or more metrics.

19. The system of claim 18, wherein the program selection circuit is configured to adjust the relationship for the patient based on a default relationship using the received at least one of the environmental information or the biopsychosocial information of the patient.

20. A non-transitory computer-readable storage medium including instructions, which when executed by a system, cause the system to perform a method for delivering neurostimulation from a stimulation device to a patient, the method comprising:

communicating with the stimulation device using a programming device configured for use by the patient;

storing a plurality of neurostimulation programs in the programming device, the neurostimulation programs each defining a pattern of neurostimulation pulses using a set of stimulation waveforms and stimulation fields;

receiving at least one of environmental information or biopsychosocial information of the patient using the programming device; and controlling the delivery of the neurostimulation using the programing device, including:

selecting a neurostimulation program from the stored plurality of neurostimulation programs based on the received at least one of the environmental information or the biopsychosocial information of the patient;

presenting a recommendation for applying the selected neurostimulation program using a user interface of the programming device;

waiting to receive a user command responding to the presented recommendation using the user interface, and communicating to the stimulation device to deliver the neurostimulation according to the selected neurostimulation program in response to the recommendation being presented for a specified time interval without receiving the user command.

* * * * *